(12) United States Patent
Henkel et al.

(10) Patent No.: US 10,605,718 B2
(45) Date of Patent: Mar. 31, 2020

(54) ARRANGEMENT FOR INDIVIDUALIZED PATIENT BLOOD ANALYSIS

(71) Applicants: Leibniz-Institut Fuer Photonische Technologien e.V. (IPHT), Jena (DE); Universitaetsklinikum Jena, Jena (DE)

(72) Inventors: Thomas Henkel, Jena (DE); Michael Bauer, Jena (DE); Ute Neugebauer, Jena (DE); Juergen Popp, Jena (DE)

(73) Assignees: Leibniz-Institut Photonische Technologien E.V., Jena (DE); Universitaetsklinikum Jena, Jena (DE)

( * ) Notice: Subject to any disclaimer, the term of this patent is extended or adjusted under 35 U.S.C. 154(b) by 0 days.

(21) Appl. No.: 15/759,066

(22) PCT Filed: Aug. 15, 2016

(86) PCT No.: PCT/DE2016/100362
§ 371 (c)(1),
(2) Date: Mar. 9, 2018

(87) PCT Pub. No.: WO2017/041782
PCT Pub. Date: Mar. 16, 2017

(65) Prior Publication Data
US 2019/0049359 A1 Feb. 14, 2019

(30) Foreign Application Priority Data

Sep. 11, 2015 (DE) .................. 10 2015 115 342
Sep. 11, 2015 (DE) .................. 10 2015 115 343
Sep. 11, 2015 (DE) .............. 20 2015 104 827 U

(51) Int. Cl.
*G01N 15/14* (2006.01)
*B01L 3/00* (2006.01)
(Continued)

(52) U.S. Cl.
CPC .... *G01N 15/1459* (2013.01); *B01L 3/502715* (2013.01); *B01L 3/502776* (2013.01);
(Continued)

(58) Field of Classification Search
CPC .................................................. G01N 15/1459
(Continued)

(56) References Cited

U.S. PATENT DOCUMENTS

| 2004/0043506 A1 | 3/2004 | Haussecker et al. |
| 2007/0153268 A1 | 7/2007 | Panza et al. |

(Continued)

FOREIGN PATENT DOCUMENTS

| DE | 10334341 A1 | 3/2004 |
| DE | 10 2004 034354 B3 | 2/2006 |

(Continued)

OTHER PUBLICATIONS

SEO, Sungkyo [et al.]: Lensfree holographic imaging for on-chip cytometry and diagnostics. In: Lab on a Chip, vol. 9, 2009, No. 6, S. 777-787. ISSN 1473-0197.
(Continued)

*Primary Examiner* — Tarifur R Chowdhury
*Assistant Examiner* — Omar H Nixon
(74) *Attorney, Agent, or Firm* — Norris McLaughlin, P.A.

(57) ABSTRACT

An arrangement for the individualized in-vitro patient blood analysis includes a holography module, a Raman spectroscopy module, a biomarker module and a flow controller which are connected in a data and information transmitting manner to a central control and computer unit, which has an information transmitting connection to a database, wherein the modules are fluidically connected to a common blood sample supply and supplies for fluid other than blood via the flow controller.

6 Claims, 5 Drawing Sheets

(51) Int. Cl.
*G01N 35/10* (2006.01)
*G01N 15/10* (2006.01)

(52) U.S. Cl.
CPC ......... *G01N 15/1463* (2013.01); *G01N 35/10* (2013.01); *B01L 2300/0816* (2013.01); *B01L 2300/0874* (2013.01); *B01L 2300/0887* (2013.01); *B01L 2400/0424* (2013.01); *B01L 2400/0487* (2013.01); *G01N 2015/1006* (2013.01); *G01N 2035/1032* (2013.01); *G01N 2035/1034* (2013.01)

(58) Field of Classification Search
USPC .......................................................... 356/73
See application file for complete search history.

(56) References Cited

U.S. PATENT DOCUMENTS

| | | |
|---|---|---|
| 2007/0177458 A1 | 8/2007 | Meiners et al. |
| 2007/0269836 A1* | 11/2007 | McPherson ........ G01N 33/6893 435/7.4 |
| 2008/0117416 A1 | 5/2008 | Hunter et al. |
| 2009/0194705 A1 | 8/2009 | Kiesel et al. |
| 2011/0165558 A1 | 7/2011 | Popp et al. |
| 2014/0234949 A1 | 8/2014 | Wasson et al. |
| 2014/0327944 A1 | 11/2014 | Naidoo et al. |
| 2015/0025348 A1* | 1/2015 | Grabowski ........ G01N 33/4905 600/369 |
| 2015/0132742 A1* | 5/2015 | Thuo ................. B01L 3/502707 435/5 |

FOREIGN PATENT DOCUMENTS

| | | |
|---|---|---|
| DE | 102008047240 A1 | 4/2010 |
| DE | 10 2012 016318 A1 | 2/2014 |
| DE | 102013015033 A1 | 3/2015 |
| WO | 2008/052221 A2 | 5/2008 |

OTHER PUBLICATIONS

Krause, Mario [el al.]: Localizing and identifying living bacteria in an abiotic environment by a combination of raman and fluorescence microscopy. In: Analytical Chemistry, vol. 80, 2008, No. 22. S/ 8568-8575. ISSN 0003-2700.

Xia H.M. et al.: Chaotic micromixers using two-layer crossing channels to exhibit fast mixing at low Reynolds numbers. In: Lab Chip, 5, 2005, 748-755.

Institut fuer Photonische Technologien e.V.: Pressemitteilung - Weniger Blut, mehr Informationen. Nov. 19, 2013. URL:http://www.leibnizipht.de/uploads/media/IPHTPresse2013_Hemospec_Medica.pdf [abgerufen am 08.06.2016] (with machine translation).

* cited by examiner

ARRANGEMENT FOR INDIVIDUALIZED PATIENT BLOOD ANALYSIS

BACKGROUND OF THE INVENTION

The invention relates to an arrangement for the individualized patient blood analysis, for sepsis tests in particular.

According to the current state of technology, larger amounts of blood are taken from the patient to be examined in clinical diagnostics in order to subsequently subject the blood samples to a wide variety of analyses which are often carried out at different laboratory workstations or even in different laboratories.

If infectious diseases are suspected, for example, blood counts are taken to determine the number and form of cellular blood components, tests are carried out with diverse specific biomarkers to qualify and quantify different infectious agents (usually, each biomarker has to be measured in a separate test) and microbiological analyses are made by cultivation and subsequent characterization of the agents These common/established clinical examinations have the disadvantage that several individual tests requiring several milliliters of patient blood have to be carried out and are, in addition, often very time-consuming (microbiological test results are often only available after two or more days) and, usually, they do not provide all relevant information (e.g. information on the activation state of the leukocytes is not currently gathered).

A simple system solution based on biomarkers, which provides the full range of information required by the physician, could not yet be provided either.

WO 2008052221 A2 discloses the application of coherent RAMAN processes for medical diagnostic and therapeutic purposes, providing a system and method to allow the non-invasive, in vivo and real-time molecular identification and quantification of molecular species in a sample or in an animal.

This method makes a non-invasive, quantitative, continuous identification of molecular species in real time possible, for example, to follow the therapeutic process.

SUMMARY OF THE INVENTION

The object of this invention is to provide an arrangement for the individualized in vitro analysis of patient blood samples, especially for sepsis tests, which avoids the disadvantages of the current state of technology and allows to obtain a meaningful test result on the basis of a blood volume of only 1 to 2 ml in less than one hour.

According to the invention, this task is solved by the characteristic features of the first patent claim. Further advantageous embodiments of the invention are described in the subclaims.

The essence of the invention is that the arrangement for the individualized patient blood analysis, especially for sepsis tests, simultaneously comprises a holography module, a Raman spectroscopy module and a biomarker module, which have an information and data transfer connection to a central control and computer unit that has an information transfer connection to a database, wherein this arrangement makes a multimodal and very fast blood analysis possible.

The three modules of the arrangement are microfluidic systems, each of them consisting of a sample preparation cartridge and a sample measurement unit, wherein the cartridges are fluidically connected to diverse fluid supplies (including a central blood sample supply) via an integrated microfluidic flow controller, which has also a data and information transfer connection to a central control and computer unit.

The integrated microfluidic flow controller makes it possible to input the sample to be analyzed at only one loading position and then distribute it automatically for the individual sample preparation cartridges and sample measurement units.

This modular design of the arrangement offers, among others, the following advantages:
- decoupling of the modules from each other with respect to optical and electrical disturbances
- optimum short distances within the modules
- easy replacement by enhanced modules
- easy servicing
- combination of different technologies with integrated evaluation.

Due to the modular, microfluidic design, a multimodal analysis of smallest amounts of patient blood (only about 1-2 ml) is possible for the stratification of patients (e.g. of patients with and without infection as well as with and without hyper-inflammatory immune response), wherein the final results provided by the modular arrangement are available much faster than in methods of the current state of technology (in less than 1 hr.) and at the same time offer the physician deeper insights into the clinical picture and differentiation possibilities.

BRIEF DESCRIPTION OF THE DRAWINGS

The invention will be explained in more detail in the following by means of the schematic drawings and the embodiment. They show.

DETAILED DESCRIPTION OF THE INVENTION

Figure 1:
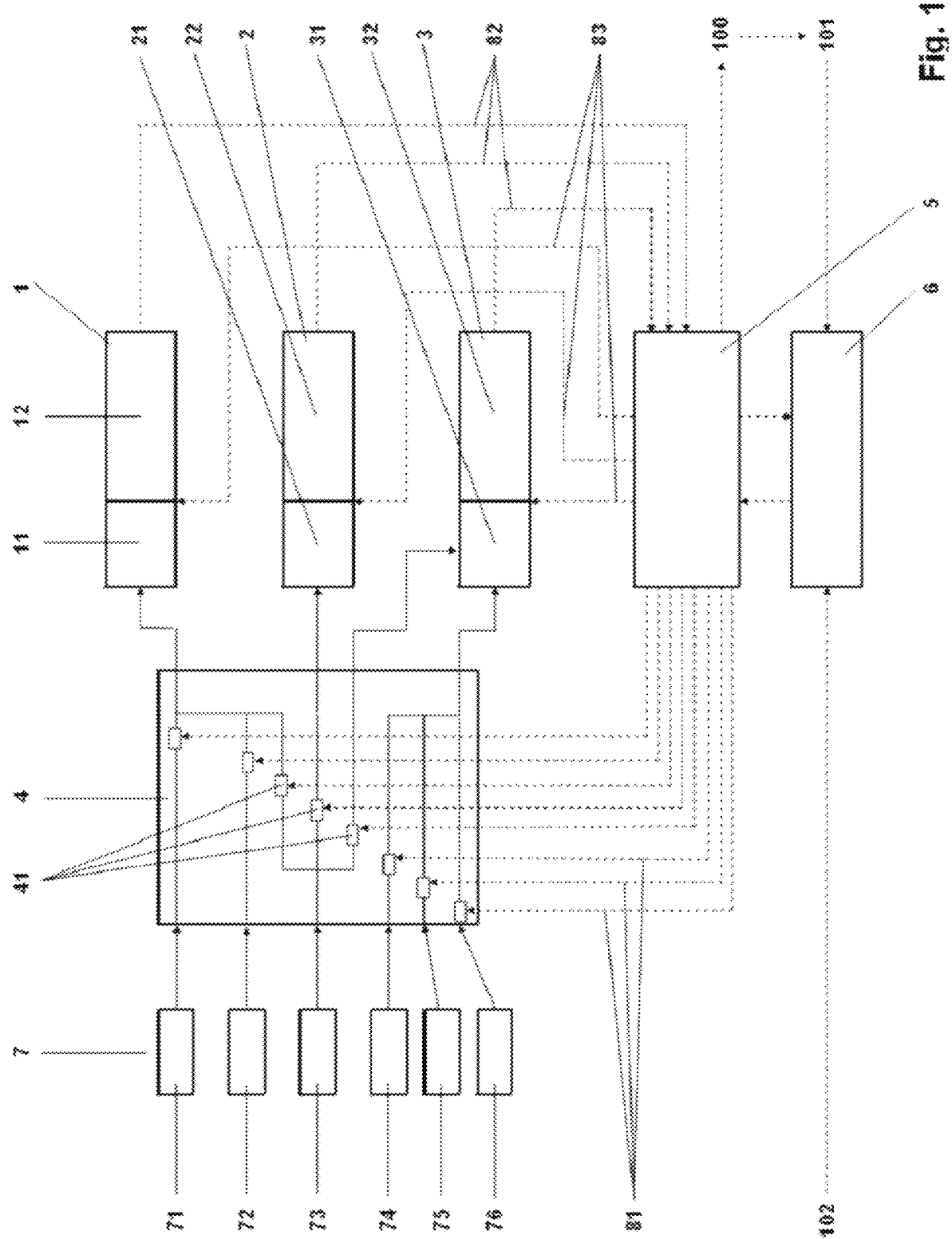
FIG. 1: a schematic drawing of an embodiment of the arrangement for the individualized patient blood analysis.

The arrangement for the individualized patient blood analysis shown in FIG. 1 comprises a holography module (1), a Raman spectroscopy module (2), a biomarker module (3) and an integrated flow controller (4) which have a data and information transfer connection to a central control and computer unit (5) which is connected to a database (6) for information exchange.

The holography module (1), the Raman spectroscopy module (2) and the biomarker module (3) are connected micro-fluidically to a common blood sample supply (73) and further fluid material supplies (7) via the flow controller (4) which preferentially consists of one unit or of several fluidically coupled units.

These further fluid material supplies (7) are a color solution supply (71), a buffer supply (72), a blood sample supply (73), a biomarker 1-supply (74), a biomarker 2-supply (75), a biomarker 3-supply (76) and supplies for service and cleaning liquids (78).

The holography module (1) consists of a holography sample preparation cartridge (11) and a holography sample measurement unit (12) which are microfluidically connected to each other.

The Raman spectroscopy module (2) consists of a Raman spectroscopy sample preparation cartridge (21) and a Raman spectroscopy sample measurement unit (22) which are microfluidically connected to each other.

The biomarker module (3) consists of a biomarker sample preparation cartridge (31) and a biomarker sample measurement unit (32) which are microfluidically connected to each other.

The flow controller (4) can consist of hoses and/or a micro-structured substrate with microfluidic channels in which controllable valves (41) are provided so that organized/well-arranged fluid guiding paths can be generated such that the fluid guiding path from the common blood sample supply (73) is split into three fluid guiding paths which lead to the cartridges (11, 21 and 31), wherein the fluid supplies (7) can be selectively connected via the valves (41) which are controlled by the control and computer unit (5). The valves (41) can be arranged in a valve block and be designed, for example, as squeeze valves.

The fluid controller is designed as an elastomer chip system (multi-layer chip system) with integrated reagent reservoirs, transport channels, a valve block and a connection block for the fluid connectors to the analysis modules and optionally integrated filter structures for separation tasks.

The fluid transport is based on the principle of slip-free linear peristaltic pumps. They convert a feed rate into a defined volume flow rate.

Therefore, the integration of additional sensors for flow rate measurement and control is not necessary any longer.

Useful monitoring functions, such as the test of the bubble-free condition of the transported fluid as well as the evaluation of filtration processes and dyeing procedures in the cartridge are optionally provided on the flow controller (4) (not shown in FIG. 1).

Contactless imaging processes are provided, for example, for the production of the flow controller (4) and can be integrated as a non-contact sensor and monitoring system for function control when optically transparent materials are used for the base plate. For this purpose, an optical monitoring system must be integrated in the system underneath the chip cartridge so that an appropriate installation space and optical accessibility for the image-supported monitoring of the system function are provided.

The elastomer chip system consists of a rigid, optically clear/transparent base plate (e.g. made of glass or plastics) against which an molded elastomer part/elastomer molded part is arranged in a liquid-tight manner which comprises the reagent reservoirs, connection channels, transport channels, filter elements, valve elements of the valve block and the connection block for the fluid connectors as well as optional filter elements and auxiliary structures for the efficient mixing of fluids. The size of the chip system can be designed, for example, in the "check/credit card format".

The base plate is a plate made of inelastic, optically transparent material and is used as carrier for the molded elastomer part and is permanently connected to it by gluing/bonding.

The materials of the base plate can be glass, silicon, metals, thermoplastic polymers (polycarbonate, COC, PVC, polystyrene), thermosetting polymers (e.g. electronic circuit boards) or ceramic carriers (LTCC and ceramic plates).

The molded elastomer part is produced, for example, by means of replication techniques (injection die molding, molding of a master of PDMS, silicone rubber or silicone materials=elastomer materials with shore hardness in the range from 10 to 120).

The molded elastomer part is joined to the base plate by gluing or bonding. If a molded elastomer part made of PDMS and a base plate made of glass are used, automatic bonding of the molded parts after surface activation by means of oxygen plasma is recommended.

The transport channels are preferentially designed as semicircular linear channels which are activated by utilizing the operating principle of linear peristaltic pumps. For this purpose, a plunger is pressed on the upper side of the chip above the transport channel to be actuated in such a manner that it is completely pinched off at the press-fit point. When the plunger is moved along the channel direction, the fluid follows the plunger and is thus transported.

The flow rate Q results from the feed rate of the plunger u and the cross section of the transport channel A to $Q=A*u$. The transport channel is connected to a fluid reservoir on one side and leads into the valve block on the opposite side. The channel dimensions range from 0.3 to 6 mm (width) and 0.15 to 3 mm (height).

The connection channels are integrated in the molded elastomer part and, compared to the transport channels, they have smaller channel cross sections with channel widths ranging from 0.1 and 1.2 mm and channel heights ranging from 0.05 and 0.8 mm.

The reagent reservoir is designed as a cavity integrated in the molded elastomer part and optionally equipped with a septum. The volumes are in the range from 5 µl to 500 µl (e.g. for service and cleaning liquids).

The valve block is implemented by an arrangement of squeeze valves. At each valve position, a valve plunger is provided which can be lowered and thus squeezes the elastomer channel and closes it positively.

The arrangement is designed such that fluids can be led from any inlets into the valve block to any outlets of the valve block. The inlets can also be operated bi-directionally as outlets of the valve block.

Figure 2:
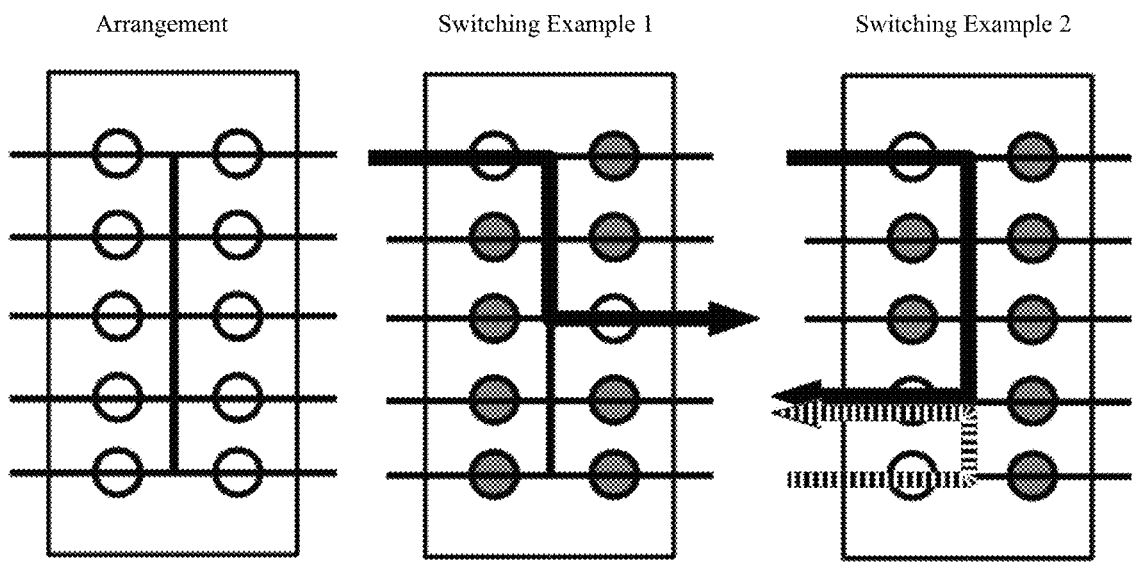
FIG. 2: a schematic drawing of a valve block of a flow controller of the arrangement according to FIG. 1 with two switching examples.

The corresponding exemplary wiring diagram of a valve block is shown in FIG. 2.

In this way, fluids from transport channels can be led to any outlet, as shown in FIG. 2, switching example 1, or, in the case of parallel transport, as shown in FIG. 2, switching example 2, they can be combined with each other from several transport channels and either collected in one transport channel or conveyed as a mixture to the analysis stations via one of the chip-side outlets.

Thanks to this simple implementation it is possible to combine fluid transport with flexibly configurable sample preparation steps.

The connection block consists of an arrangement of vertical fluid outlets integrated in the chip cartridge, which are fluidically connected to the valve block. The fluidic contact is produced by pressing-on a connection plate which contains the connection capillaries and a sealing element.

The connection plate can be automatically lowered to the connection position or lifted and thus makes a releasable fluidic connection of the flow controller 4 to the system and analysis modules (1, 2 and 3) possible.

The filter elements are column arrays integrated in channels or filter membranes integrated in the connection channels or commercially available filter elements integrated into the installation space between two transport or connection channels.

Furthermore, auxiliary structures are provided for efficient mixing of fluids. As a result, efficient mixing is achieved in the delivery channels by pumping the fluid into the fluid reservoirs and pumping it back into the transport channels.

In addition, the fluid can be agitated and used for mixing by periodically lowering the plunger onto the transport channel.

Moreover, micro-mixers known per se based on the multi-lamination principle can be integrated into the cartridge.

In a fluid management system with high flow rates and Reynolds numbers, commonly known micro-mixers based on the principles of chaotic advection, such as T-mixers or meander mixers, can be used. These systems operate above a critical Reynolds number as mixers (Re>240 for T mixers and Re>80 for zigzag mixers) and can be used when fluids shall be transported at high velocities and with high Reynolds numbers.

In a fluid management system with low flow rates and small Reynolds numbers (Re<10), a special fluid rotation unit consisting of two or more microchannel segments, which are arranged one behind the other and connected to each other at their ends, is inserted in the flow controller (4), wherein always the two channel segments connected to each other are arranged at an angle α to each other, the two channel segments connected to each other are provided at two levels one positioned on top of the other, the ends of the channel segments are closed, and the transition to the next channel segment is located laterally at the channel segment ends. The channel segments arranged one behind the other are alternately inserted into the upper and lower chip layer.

A hydrodynamic focusing unit can also be inserted into this two-layer chip system in front of and/or behind the fluid rotation arrangement.

As the channel segments are arranged at an angle to each other, the medium flowing through them is subject to directional changes which altogether cause a rotation of the medium around the axis in flow direction so that this fluid rotation unit is used when the fluids are to be transported at low velocities and with small Reynolds numbers.

The special fluid rotation unit is characterized by flow channel segments in the form of microchannels which are arranged at an angle to each other and one behind the other in a two-layer chip system, wherein the fluid flow, when flowing through the transitions between the channels, is rotated around the flow axis by an angle α which depends on the channel geometry and the angle β between the channel segments, wherein this angle β indicates the deviation from a linear or parallel arrangement of the connected channel segments.

For the variety of possible channel geometries, in particular the shape of the channel cross-sections, and of the possible formations of the transitions between the channel segments, it is possible to calculate the resulting angle of fluid rotation by applying a CFD (computational fluid dynamics) method. This is exemplified by a semicircular channel cross-section, a hemispherical channel segment end and a congruent transition between the channel segments.

For professionals, software systems for the implementation of this modeling are available both as part of commercial CAD systems (e.g. SolidWorks) and as separate systems from commercial providers (e.g. Ansys, Fluent, COMSOL) or as open source toolkits (e.g. OpenFoam). The application of the underlying numerical finite element methods is an integral part of university education in engineering study courses and is therefore familiar to trained experts.

Figure 3:
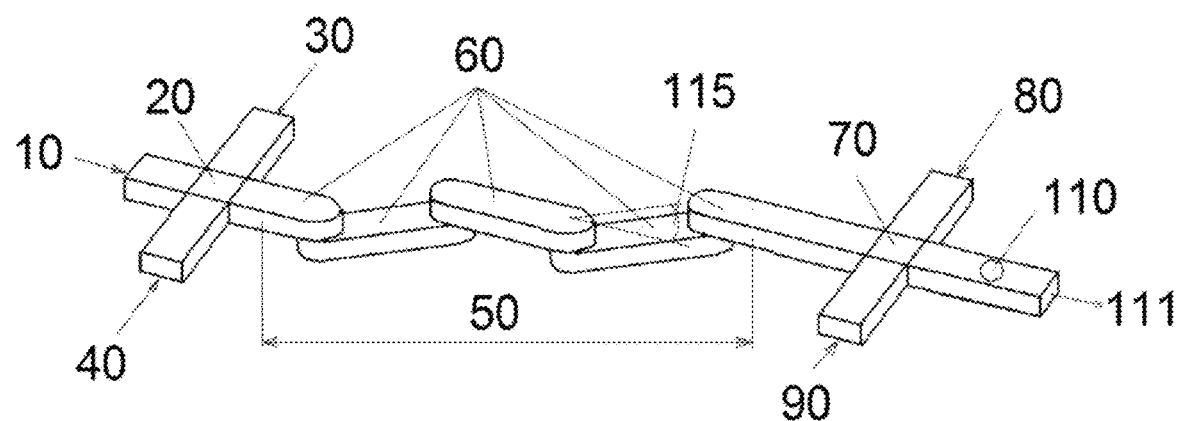
FIG. 3: a schematic drawing of an embodiment of the arrangement for fluid rotation in a flow controller of the arrangement according to FIG. 1 for three-dimensional hydrodynamic focusing.
Figure 4:
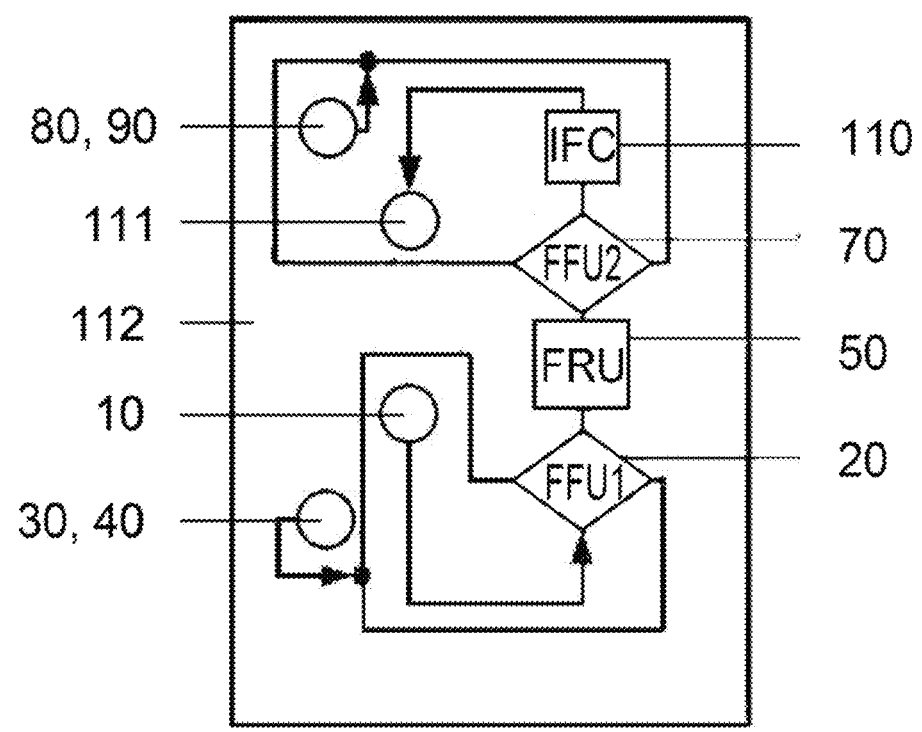
FIG. 4: a schematic drawing of an embodiment of the two-layer chip system of the arrangement according to FIG. 3, FIG. 5: a schematic drawing of the cross sections of the fluid channels in the two-layer chip system according to FIG. 4, FIG. 6: a schematic drawing of an embodiment of the arrangement for fluid rotation as a part of a flow controller for three-dimensional hydrodynamic focusing.
Figure 5:
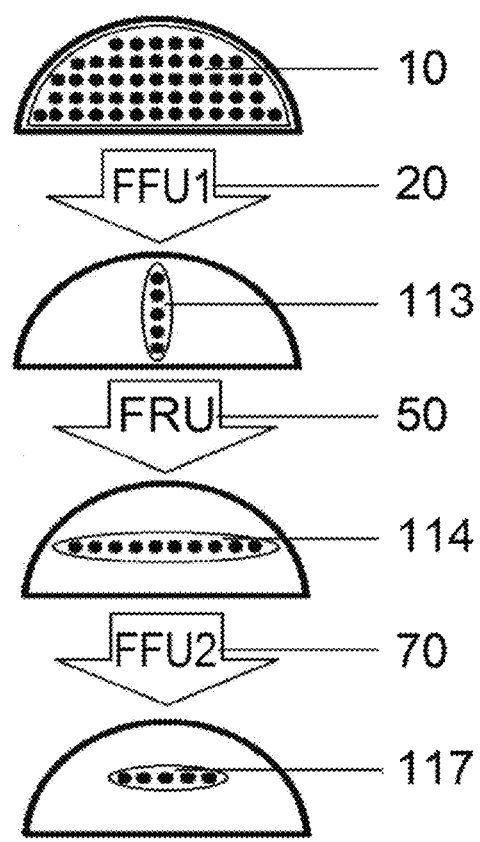
Figure 6:
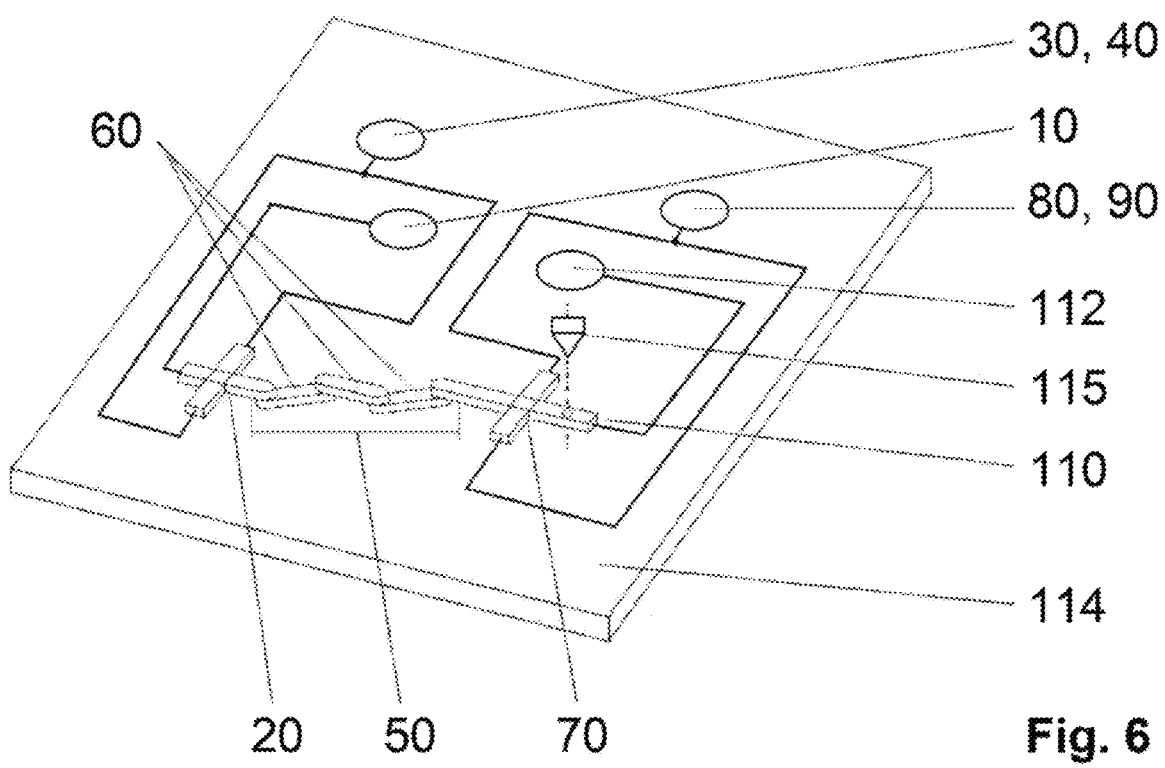

The flow controller (4) with fluid rotation unit (50) comprises the following four assemblies as shown in FIG. 3:
the first hydrodynamic focusing unit (20)
the fluid rotation unit according to this invention (50)
the second hydrodynamic focusing unit (70)
the examination channel or flow measuring cell (110), e.g. for image-based flow cytometry.

The fluid rotation unit (50) as a part of the flow controller (4) consists of two or more channel segments (60) arranged one behind the other and connected to each other at their ends, wherein always the two channel segments connected to each other are arranged at an angle to each other (and not in a straight line) (115) so that a fluid flow must always change the direction when passing the transitions between the channel segments (60).

The channel segments can be inserted in any substrate that is suitable for transporting the fluid. Preferentially, the material is optically translucent glass or optically translucent plastic material to integrate the flow measuring cell directly into the two-layer chip system. The material borosilicate glass is particularly advantageous.

In a two-layer chip system, the chip level of which shall be aligned horizontally for illustration purposes, the channel segments (60) are inserted alternately into the upper and lower substrate such that after the two chip layers have been connected the previously open channels are closed by the surface of the respective other chip layer and a connection to the next channel segment is only given at the ends of the channels (see FIG. 3).

The cross-section geometry of the channels and the design of the channel ends and transitions result from the possibilities offered by the technologies used for channel production. In principle, semicircular channel cross-sections in conjunction with end pieces, which are designed as ball segments or have similar geometries, are recommended (see FIGS. 7 and 8).

In addition, channels with round geometries or with geometries that can be described by circular segments or geometries similar to them (ellipse segments, combinations of circular segments and trapezoids or triangular surfaces) can be used. Moreover, trapezoidal or rectangular channel cross-sections can be used in conjunction with end pieces which can be illustrated by rotating bodies of these geometries or by geometries approximating them and being composed of partial areas.

When the fluid flows through such a transition, for example, from top to bottom (see FIGS. 7 and 8), the fluid is first diverted downwards (221) at the end of the upper channel segment (220). At the beginning of the adjacent channel segment (224), the fluid flow is immediately diverted again and led into the lower channel segment (223). Due to the proximity of the two channel segment ends, the two changes in direction merge and can only be considered in combination. This aspect is a clear difference to the state of the art in which transfer channels in intervening middle chip layers are used so that two separate directional changes can be differentiated.

As the two connected channel segments are arranged at an angle to each other (and not in a straight line or parallel to each other) (115), a rotation of the fluid around the flow axis is produced.

It is possible to arrange several transitions one behind the other, wherein the rotations sum up. In such an arrangement, a fluid lamella follows a Moebius-strip-like flow path. It must be ensured that the direction of the transitions is maintained, otherwise the rotations will subtract one from the other or cancel each other out.

In order to achieve a desired total rotation of the fluid by 90 degrees, for example with a semicircular channel cross-section with a channel height of 70 μm and a length of the channel segments (15) of 600 μm, six transitions with an articulation angle of β=32 degrees can be arranged one behind the other in such a way that a total fluid rotation by 90 degrees is obtained.

Figure 7:
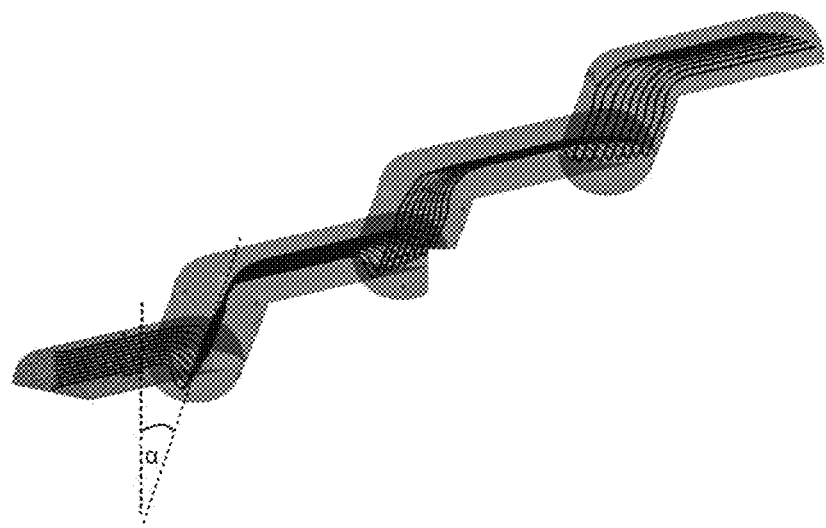
FIG. 7: a first schematic drawing for the schematic representation of fluid rotation in a flow controller.
Figure 8:
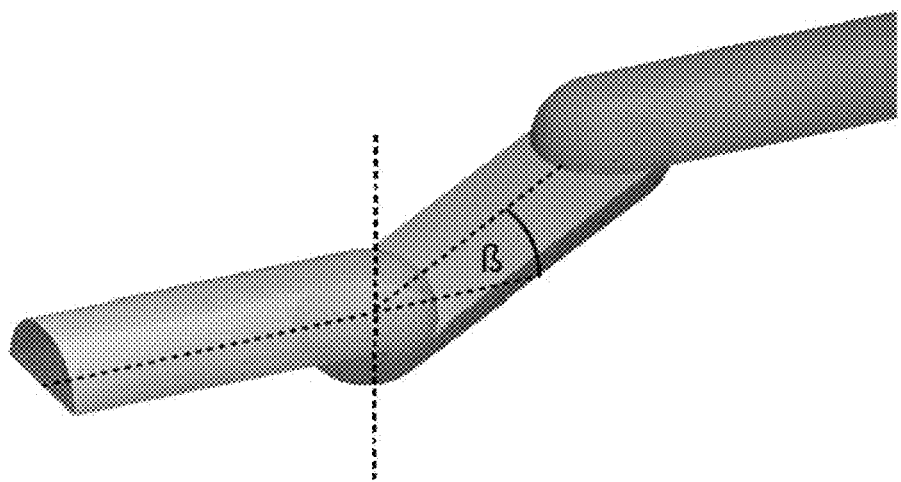
FIG. 8: a second schematic drawing of an embodiment of fluid rotation in a flow controller.

In FIGS. 7 and 8, the articulation angle of the channels B and the angle of axial rotation a are plotted as an example for illustrative purposes. In the specific case, the desired fluid rotation by 90 degrees is achieved after passing six channel transitions with an articulation angle of 32 degrees to each other. Herein, the rotation angle α of the fluid lamella is not consistent in the individual transitions but rather depends on the articulation angle ß and the respective orientation of the incoming lamella.

The substrate (112) is part of the flow controller (4) and is made, for example, of glass or plastics and is designed in the form of a two-layer chip system, wherein the inlets (10, 30, 40, 80, 90) for the sample and auxiliary fluid supply can be connected to suitable pumps, such as syringe pumps, peristaltic pumps or pressure-driven fluid transport systems, such that fluids can be transported.

When the fluid rotation unit is used as intended in a two-layer chip system of the flow controller, it is operated as follows:

The fluid to be tested is introduced into the sample supply (10) and the auxiliary fluids for the hydrodynamic focusing units are introduced into the corresponding inlets (30, 40, 80, 90) by means of suitable pumps, such as syringe pumps, peristaltic pumps or pressure-driven fluid-transporting systems In the first hydrodynamic focusing unit (20) the auxiliary fluids (30, 40) are supplied under such a pressure that a fluid lamella orientated perpendicularly on the chip level is formed from the sample fluid. This lamella further flows into the fluid rotation unit (50).

Always one rotation takes place when the transitions between the channel segments (6) are passed.

The embodiment shown in FIGS. 7 and 8 includes six channel segment transitions the channel segments of which are arranged at an angle 1 (115) of 32 degrees to each other. Thus, the fluids rotate a total of six times. The total angle of the fluid rotation of 90 degrees results from the sum of the combination of the partial angles.

The fluid lamella previously perpendicularly orientated on the chip level leaves the chip rotated by this angle around the transport axis of the fluid and is now positioned parallel to the chip level (114).

In the second hydrodynamic focusing unit (70), the auxiliary fluids (80, 90) are supplied at such a pressure that the fluid lamella orientated parallel to the chip level is slightly compressed to obtain a homogeneous fluid lamella (117) which is not influenced by the channel walls. Thus, the three-dimensional hydrodynamic focusing is completed.

The fluid lamella (117) formed in this way can then be led in the examination channel or in the flow measuring cell (110) to an imaging procedure, e.g. an image-based flow cytometry in the holography module (1), or the fluid can be led out at the sample outlet (111) and led into the correspondingly following modules, the spectroscopy module (2) and the biomarker module (3).

Fluid rotation in a fluid management with low flow rates has the advantage that a complete three-dimensional hydrodynamic focusing can be realized in a single two-layer chip system of the flow controller (4). Another advantage of fluid rotation in a fluid management with low flow rates is that fluid rotation in the flow controller (4) can be performed at low transport velocities in a strictly laminar transport regime dominated by viscous forces and characterized by small Reynolds numbers. Therefore, the system can be used for low flow rates and transport velocities of just a few millimeters per second. The thus reduced motion blur allows, in contrast to established FACS systems with transport velocities in the range of up to 1 m/sec, comparatively long exposure times of up to 20 msec without identifiable motion blur.

Thus, the flow controller (4) offers optimal conditions for fluorescence imaging flow cytometry in the holography module (1) or biomarker module (3) and image-based recording of low-intensity optical signals while avoiding motion blur during examinations in the holography module (1), spectroscopy module (2) and biomarker module (3).

Another advantage of fluid rotation in the flow controller (4) is the compatibility with smaller Reynolds numbers. A variety of alternative methods for hydrodynamic focusing utilizes inertial effects of fluids on geometric structures integrated in the channel. These include jet formation on nozzles or the use of Dean flow effects in curved channels. These effects are produced with Reynolds numbers in the range between 50 and 500, and the quality of the resulting effects shows a strong dependence on transport velocity. For highly viscous fluids, the required Reynolds numbers in microchannels can sometimes only be achieved with high-pressure pumping systems due to the high fluidic resistances.

By contrast, fluid rotation in the flow controller (4) with the rotation angle α over the entire flow rate range dominated by viscous forces with Re<10 is independent of the transport velocity.

It is often necessary to adjust the density of the process fluids to the density of the biological particles to be tested. For biological particles with a density of approximately 1.25 g/ccm, this adjustment can be achieved, for example, by using a 50% solution of cane sugar. Polysaccharides, e.g. Ficoll-400, are often added to adjust the density of cells with densities in the range between 1.005 and 1.2 g/ccm.

All these additives cause a highly significant increase in viscosity by a factor of up to 20 (30% Ficoll). Even under these conditions, the correct function of the flow controller (4) with respect to the fluid rotation achieved is maintained unchanged.

When fluid rotation is performed in the flow controller (4), microchannels with a diameter ranging from 2 μm to 0.75 mm are used. They can be operated at flow rates of between 1 pl/sec and 4 μl/sec in the sphere of the fluid rotation unit (50). For channels with a diameter of 0.75 mm, the maximum flow rate for water with a dynamic viscosity of 0.001 Pas within the fluid rotation unit (50) is about 4 μl/sec with a Reynolds number of 10. In exceptional cases, the systems can be operated with Reynolds numbers up to 50 with slight limitations in function. The upper limit for the flow rates to be applied can then be indicated as 20 µl/sec. The specific suitability of the process parameters used in conjunction with the density and viscosity of the carrier fluids can be verified by means of the Reynolds number. It is recommended to use the respective hydraulic diameter of the channels as characteristic dimension D.

$$Re = rho * U\_MEAN * D\_H / mu$$

with rho: density, U_MEAN: mean transport velocity, D_H: hydraulic diameter, and mu: dynamic viscosity.

The minimum possible flow rate is only defined by the technical possibilities of the pump systems used and can be specified in the range of one picoliter per second.

A further possibility for an efficient mixing in the flow controller (4) is the fluid introduction through a nozzle into a cavity known per se. This arrangement generates circular flow patterns in the cavity which lead to efficient mixing and at the same time counteract sedimentation of particles and cells contained in the fluid.

The central control and computer unit (5) is provided with an integrated control software which controls and regulates all processes.

The holography sample preparation cartridge (11) comprises microstructured fluidic lysis channels or dielectrophoresis channels with microelectrodes which are connected to the flow controller (4) in a micro-fluidic manner.

Examples of parameters for operating the flow controller (4) are:
 provision of flow rates in the range from 0.1 to 10 nl/sec during measurement
 provision of flow rates of up to 10 µl/sec for cleaning and service operations
 provision of flow rates in the order of magnitude of 1 µl/sec for fluid exchange in the connection capillaries
 application of a defined counter pressure to the outlets to capture the cells at the pore arrays for Raman measurement.

The operation of the three modules [holography module (1), Raman spectroscopy module (2) and biomarker module (3)] is simultaneously started by the central control and computer unit (5) just after the sample has been loaded into the blood sample supply (73) so that a parallel operation of the three sample measurement units is given in order to keep the time required for diagnostic testing as short as possible The holography sample measurement unit (12) is an arrangement for a lensless inline incident reflected-light microscope with a coherent illumination source and a detector array, as known, for example, from DE 10 2012 016 318 A1.

The Raman spectroscopy sample preparation cartridge (21) comprises microstructured fluidic lysis channels or dielectrophoresis channels with microelectrodes which are microfluidically connected to the flow controller (4).

The electrode structures required are integrated into the respective cartridge and the system is electronically triggered such that the electrodes are generated on the carrier substrate of the cartridge by means of thin-film processes and photolithography/electron beam lithography.

The Raman spectroscopy sample measurement unit (22) is, for example, a portable Raman spectroscopy system for mobile use, as known from DE 10 2004 034 354 B3.

A lab-in-a-vial platform is used as a sample preparation cartridge for the plasma separation from whole blood. This cartridge contains a closable, cylindrical vessel with a diameter in the range between 5 and 25 mm with a conical or round-tapering bottom tip. The side walls of the vessel are equipped with catching structures for blood cells.

For separation, the cylindrical vessel is rotated around its axis. The angular velocity required results from the centrifugal accelerations mentioned for blood cell separation in literature and from the diameter of the vessel.

The blood cells are introduced by the centrifugal forces into the catching structures coating the side walls.

The cell-free plasma overlays the catching structures in form of a fluid film.

After the completion of rotation, this film sinks downwards under the influence of gravity and accumulates in the tip of the cylindrical vessel, from where it is either manually pipetted or automatically removed by means of an autosampler.

Whereas in conventional centrifugation the plasma has to be pipetted off as supernatant from the cells accumulated in the lower part of the vessel, in the method described here a pure plasma sample is collected in the tip of the vessel, which can be removed completely and fully automatically, e.g. by the needle of the autosampler. Thus, this approach offers optimal conditions for automated plasma separation.

Thanks to the short sedimentation paths (only a few millimeters—compared to several centimeters in conventional vacutainers), the process time required is reduced to 4 minutes (including loading the vessel and removing the plasma).

The catching structures for blood cell separation are designed as three-dimensional surface structures with recesses into which the blood cells are introduced during centrifugation and which prevent the blood cells from flowing away under the influence of gravity.

In the simplest case, polyester gauze pieces with a mesh width in the range between 30 and 200 µm and a thickness of 200 µm can be placed on the side walls of the vessel. During centrifugation, they press themselves automatically against the wall and thus form the desired catch structures.

Alternatively, recesses with structure widths of between 30 and 200 µm and depths of up to 200 µm can be provided in the side walls.

Another possibility is the integration of column structures with a gap ranging between 30 and 300 µm and a height ranging from 100 to 500 µm.

For plasma separation, commercially available 2 ml disposable reaction vessels with a round bottom made of polypropylene are used. A gauze is used as an example of a catching structure.

The biomarker sample preparation cartridge (31) comprises microstructured fluidic dielectrophoresis microchannels with microelectrodes or structured microchannels with mechanical filters or cross-sectional changes, which are microfluidically connected to the flow controller (4).

All cartridges in the modules (1, 2 and 3) can be designed both as disposable and reusable cartridges, wherein the disposable cartridges are made of plastics (which is inexpensive) and the reusable cartridges with optical functions are made of glass, in particular quartz glass, and can be cleaned so that these expensive cartridges are regenerated after each sample cycle in intermediary cleaning steps.

The biomarker sample measurement unit (32) is a photo sensor detector array arrangement with a coherent illumination source, which is used for example for the detection of diagnostic and prognostic markers in biomedicine.

It is a chip-based biomarker detection based on an optically readable, surface-bound immunofluorescence assay. Other alternatives of biomarker detection known per se can also be used.

The central control and computer unit (5) is provided with an integrated software control system for regulating all processes of the flow controller (4) and of all modules (1, 2 and 3) and with special software for processing and evaluating the measurement data recorded by the three modules (1, 2 and 3), for example for evaluating the Raman data.

This evaluation of Raman data with the aim of extracting clinically relevant information from the Raman spectra is carried out by using multivariate data analysis techniques, such as main component analysis, neural "networks", linear discriminant analysis or cluster analysis.

At the same time, the access of the central control and computer unit (5) to the database (6) enables the comparison of the recorded and processed data of the modules (1, 2 and 3) with the reference data stored in the database (6) and the complex data evaluation, which results in a specified score value. Here, methods known per se are applied.

The arrangement is operated as follows:

Via the blood sample supply (73), the blood sample is injected manually directly from the cannula, with which it was taken from the patient, into the microfluidic system of the flow controller (4).

Alternatively, it is also possible to supply the blood samples automatically, for example by a pipette-robot.

The blood volume of 2.7 ml from the smallest currently available cannula is absolutely sufficient, and a pretreatment of the patient is not necessary because the blood sample is directly pretreated in the corresponding microfluidic element of the three different sample preparation cartridges (11, 21 and 31) for the subsequent analysis in the down-stream sample measurement units (12, 22 and 32).

The blood sample is distributed by the flow controller (4) to the sample preparation cartridges (11, 21 and 31) as follows:

Holography Module (1)

The blood components are holographically recorded on the basis of whole blood on the one hand and on the basis of enriched leukocytes on the other hand by.

For the holographic recording of the blood components, the sample is first diluted (approx. 1:500). This is done in the flow controller (4) by adding buffers from the buffer supply (72) and then microfluidically transferring the diluted whole blood to the holography sample preparation cartridge (11).

In total, maximally 4 μl whole blood is used, diluted to a maximum of 2 ml and prepared and measured as follows:

Raman Spectroscopy Module (2)

For Raman spectroscopic analysis of white blood cells (leukocytes), the red blood cells (erythrocytes) are separated from the whole blood in the Raman spectroscopy sample preparation cartridge (21). This is 3 preferably done by lysis of the erythrocytes, e.g. with NH4Cl, but can alternatively also be done by dielectrophoretic deflection.

Then, this leukocyte-enriched blood (approx. 4 μl) is transferred to the Raman spectroscopy sample measurement unit (22).

Biomarker Module (3)

To analyze the biomarkers in the separated plasma, the cellular components of the blood are separated in the biomarker sample preparation cartridge (31). For this purpose, filtration techniques or, alternatively, deflection techniques with the aid of electric fields (dielectrophoresis) or microcentrifugation are applied.

In this step, approximately 1 ml of the total blood sample is used, wherein approximately 500 μl plasma are transferred to the down-stream biomarker sample measurement unit (32).

In the holography sample measurement unit (12), the number and form of the cellular components are recorded with a special focus on erythrocytes and leukocytes. This is done with a lensless installation in a single-channel microfluidic system. The image acquisition frequency must be adapted to the flow velocity (or vice versa).

The image acquisition is followed by an image analysis, which also allows the differentiation of different leukocyte subtypes on the basis of nuclear morphology. In order to achieve optimum results, it is also possible to subject the whole blood sample to a further pre-treatment step before analyzing the number of leukocyte subtypes, in which the numerically superior erythrocytes (approx. 1000 erythrocytes per leukocyte) are first removed from the sample by lysis or deflecting techniques with the aid of electric fields (dielectrophoresis) or microcentrifugation. To achieve a better contrast of the subtypes, it is also possible to stain the cell nucleus (e.g. with Kimura staining solution).

In the Raman spectroscopy sample measurement unit (22), the leukocytes are arranged first on a regular measuring grid for effective spectroscopic characterization.

This is achieved, for example, by means of an integrated microfluidic perforated chip structure, in which the liquid flows through holes of approximately 4 μm in size due to slight negative pressure in the chip structure. At an only slight negative pressure, the large leukocytes attach themselves to these holes and are thus available at well-defined locations for further spectroscopic characterization. Blood plates are not held back by the holes and therefore do not remain on the integrated microfluidic perforated structure.

The Raman spectra are excited by commercially available lasers, e.g. 785 nm. If borofloat glass is used for the production of micro-hole chip microfluidics, a laser in the green range (e.g. 532 nm) must be used for the excitation of the Raman spectra, as otherwise the background radiation of the glass outshines the Raman spectra of the cells.

The spectra are recorded exactly above the holes with a diameter of approximately 1 to 5 μm in order to avoid a spectral contribution of the perforated chip membrane. It is possible to record a spectrum with an expanded laser beam or to record several individual spectra in the corresponding area. Great importance is attached to a fast and parallel characterization of several cells on the chip because the analysis time can be shortened by this. A total number of at least 500 cells are analyzed.

In addition to the cells, a spectrum of the perforated membrane is always recorded. These records are used as an internal control for automated evaluation. About 1 second is required to record a single spectrum. The spectra are evaluated in the fingerprint range (approx. 600 to 1860 $cm^{-1}$). If required, the CH range (2750 to 3100 $cm^{-1}$) can also be included.

Automated evaluation includes a spectrum pre-treatment (with background correction and standardization) as well as an assignment of the spectrum to the leukocyte subtype and "activation state".

In Raman analysis, the numerous leukocytes, such as neutrophil granulocytes and lymphocytes, are of particular importance. Possible "activation states" that can be detected by the module, are: a) dormant, i.e. the patient has no infection and no inflammation, b) activated by sterile inflammation (such as may occur after surgery or myocardial infarction), c) activated by infection. In case of the last condition, a further distinction is useful which, for example, offers insights into the pathogen (fungus, bacteria, virus) and the severity of the immune response (adequate vs. exuberant, which leads to organ failure).

An established classification model, which makes use of specific spectral characteristics and changes for a better characterization of the immune response, is used for the leukocyte subtype and the leukocyte "activation state". In order to detect the leukocyte subtype, specific fluorescence staining with surface markers on the integrated microfluidic hole-chip structure is principally also possible still after Raman measurement. Then, the Raman module must be equipped with an appropriate excitation lamp and camera for the readout.

In the biomarker sample measurement unit (32), a fluorescence measurement is carried out for the determination of different biomarker concentrations in the plasma by the simultaneous analysis of at least 3 fluorescent biomarkers in a microfluidics. The selection of biomarkers includes both diagnostic markers (e.g. CRP, IL-6, PCT) and prognostic markers (e.g. suPar).

The central control and computer software (5) with access to a database (6) is also important for operating the arrangement.

On the one hand, it processes the data flow (81) for controlling the valves (41), the data flow (82) for transferring the measured values from the modules (1, 2 and 3) to the control system, and the data flow (83) for controlling the measuring processes in the modules (1, 2 and 3), and on the other hand it is used for internal data reconciliation with the database (6) and for the output (100) of the results.

The database (6) is used for the external evaluation and for the return of the results (101), e.g. control by the physician, and for the input (102) of data from external sources (specific patient data).

The control and computer software (5), which connects the individual components of the arrangement to each other to allow easy control from a user platform but also carries out an integrated multivariate data analysis so that the individual results of each analysis contribute optimally to the overall result, provides a user interface that can be easily operated by a doctor or nurse.

Just as the patient's clinical data from the hospital system which are required for statistical evaluation, the patient ID of the blood sample is read in from data of external sources via the input (102). The individual patient blood samples can be read-in and identified by barcode scanners.

The user interface documents a successful completion of the completed analyses of the individual modules (1, 2 and 3) or it displays any errors that might have occurred.

As a result, both the results of the individual modules (1, 2 and 3), i.e. biomarker concentrations, cell numbers and a Raman score, and the correlation of these individual results are displayed after being internally evaluated together with the imported clinical data by the control and computer software (5) and then displayed as a "sepsis score" for the physician.

This "sepsis score" value provides information on the probability of a patient's infection and the probability of the critical development of the patient (e.g. organ failure, septic shock), i.e. that he/she needs special medical attention.

The underlying classification model, which allows these statements to be made from the great number of parameters, is trained and evaluated by means of the external evaluation and return (101) of the results into the database of well-defined patients whose disease progression is known.

An advantage of the parallel operation of the three modules [holography module (1), Raman spectroscopy module (2) and biomarker module (3)] coupled to the flow controller (4) according the present technical solution is that, compared to the hitherto known individual solutions which only deliver the biomarker concentrations, the cell numbers or a Raman score as a result, all the individual results of the three modules are available simultaneously in a much shorter period of time, wherein the correlation of these individual results is displayed such that they are internally evaluated together with the imported clinical data by the control and computer software (5) and then evaluated and displayed as a "sepsis score" for the physician.

Another advantage is the fact that the parallel operation of the three modules (1, 2 and 3), which is made possible by the special operating mode of the flow controller (4) and by the central control and computer unit (5), produces a synergy effect so that the entire analysis [i.e. from the injection of the blood with a small blood quantity of only 1 to 2 ml until the indication of the so-called "sepsis score" as a final meaningful test result on the user interface of the control and computer software (5)] takes maximally one hour.

The advantage of this short measuring time of maximally one hour is that [in the event that the control and computer software (5) does not generate an error message] an external access to the arrangement is not necessary during this period.

It is also advantageous that, in the event that biomarker concentrations, cell numbers and Raman score provided by the modules (1, 2 and 3) do produce ambiguous or contradictory intermediate results on the "way" to the final result in the form of the "sepsis score", the control and computer software (5) provides feedback to the flow controller (4) in such a way that a new automatic throughput of the sample in question is affected by the modules (1, 2 and 3).

Moreover, the miniaturization of the holography module (1), Raman spectroscopy module (2) and biomarker module (3), the compact biomarker sample measurement unit (32) and the portable Raman spectroscopy sample measurement unit (22) allow to make an analysis directly in the vicinity of the patient (usually intensive care patient for primary application or emergency admission situation), which is a further advantage of this technical solution.

All the features explained in the description and the exemplary embodiments are considered to be within the scope of the invention, either individually or in any combination with each other.

LIST OF REFERENCE NUMERALS

1—holography module
11—holography sample preparation cartridge
12—holography sample measurement unit
2—Raman spectroscopy module
21—Raman spectroscopy sample preparation cartridge
22—Raman spectroscopy sample measurement unit
3—biomarker module
31—biomarker sample preparation cartridge
32—biomarker sample measurement unit
4—flow controller
41—controllable valve
5 central control and computer unit with integrated software control
6—database
7—fluid material supplies
71—color solution supply
72—buffer supply
73—blood sample supply
74—biomarker 1-supply
75—biomarker 2-supply
76—biomarker 3-supply
81—data flow for controlling the valves 82—data flow for transferring the measured values from the modules to the control system
83—data flow for controlling the measurement processes in the modules
100—output of results
101—external evaluation and return of the results to the database
102—input of data from external sources
10—sample supply
20—first hydrodynamic focusing unit
30—auxiliary fluid (carrier fluid) for the first focusing unit
40—auxiliary fluid (carrier fluid) for the first focusing unit
50—fluid rotation unit
60—channel segments arranged at an angle to each other
70—second hydrodynamic focusing unit
80—auxiliary fluid (carrier fluid) for the second focusing unit
90—auxiliary fluid (carrier fluid) for the second focusing unit
110—examination channel, e.g. for image-based flow cytometry
111—sample output
112—substrate of the two-layer chip system
113—fluid lamella behind the first hydrodynamic focusing unit
114—chip level
115—angle β between the channel segments
116—angle α of the rotation of the fluid around the flow axis
117—homogeneous fluid lamella (fluid lamella after fluid rotation)
220—end of a channel segment
221—deflection by 90 degrees at the end of the channel segment
222—transition between the chip layers
223—deflection by 90 degrees at the beginning of the following channel segment
224—start of the following channel segment
225—level between the two layers of the two-layer chip system

The invention claimed is:

1. An arrangement for the individualized in-vitro patient blood analysis comprising a holography module, a Raman spectroscopy module, a biomarker module and an integrated flow controller which have a data and information transmitting connection to a central control and computer unit which has an information transmitting connection to a database, wherein;

the holography module comprises a holography sample preparation cartridge and a holography sample measurement unit which are microfluidically connected to each other;

the Raman spectroscopy module comprises a Raman spectroscopy sample preparation cartridge and a Raman spectroscopy sample measurement unit which are microfluidically connected to each other;

the biomarker module comprises a biomarker sample preparation cartridge and biomarker sample measurement unit which are microfluidically connected to each other;

the holography, Raman spectroscopy and biomarker modules are fluidically connected to a common blood sample supply and supplies for fluid other than blood via the flow controller;

the holography sample preparation cartridge comprises microstructured microfluidic lysis channels or dielectrophoresis channels provided with microelectrodes, the channels of the holography sample preparation cartridge being microfluidically connected to the flow controller, and the holography sample measurement unit includes a lensless inline reflected-light microscope with a coherent illumination source and a detector array;

the Raman spectroscopy sample preparation cartridge comprises microstructured microfluidic lysis channels or dielectrophoresis channels provided with microelectrodes, the channels of the Raman spectroscopy sample preparation cartridge being microfluidically connected to the flow controller, and the Raman spectroscopy sample measurement unit is a portable Raman spectroscopy system for mobile use;

the biomarker sample preparation cartridge comprises microstructured microfluidic dielectrophoresis channels provided with microelectrodes or comprises microchannels provided with mechanical filters or cross-section changes, the respective channels or microchannels of the biomarker sample preparation cartridge being microfluidically connected to the flow controller, and the biomarker sample measurement unit is a photosensor detector array arrangement with a coherent illumination source;

the holography, Raman spectroscopy and biomarker modules, the blood sample supply and the supplies for fluid other than blood are combined in a fluidically integrated manner via the flow controller so that data flows for controlling valves, for transferring measured values from the holography, Raman spectroscopy and biomarker modules to the central control and computer unit and for controlling measurement processes in the holography, Raman spectroscopy and biomarker modules by the central control and computer unit via the flow controller; and the flow controller comprises a micro-structured substrate provided with microfluidic channels in which controllable valves are provided so that orderly fluid guiding paths can be generated so that the fluid guiding path from the common blood, sample supply is divided into three fluid guiding paths which respectively lead to the respective holography, Raman spectroscopy and biomarker cartridges, and wherein the supplies for fluid other than blood can be selectively connected via the valves which are controlled by the control and computer unit;

wherein the flow controller comprises a fluid rotation unit configured to effect fluid rotation of a liquid in laminar flow at a Reynolds number less than 10 and comprising two or more channel segments which are arranged one behind the other, closed at their ends, alternately formed in an upper and a lower chip layer of a two-layer chip system and connected to each other proximate their ends, and wherein an axis of each of the channel segments is at a respective predetermined angle β relative to an axis of each of the channel segments to which it is connected so that a fluid flow must always change its direction when passing through transitions between the channel segments; and wherein the angle β and geometry of the channel segments are selected so that at each transition from one of the channel segments to another of the channel segments lamella of the liquid in laminar flow are rotated in a same direction about an axis of direction of flow of the liquid through the transition to effect a rotation of the lamella about the axis by the fluid rotation unit of an angle α in total.

2. The arrangement for the individualized in-vitro patient blood analysis according to claim 1, wherein the angle α is 32 degrees.

3. The arrangement for the individualized in-vitro patient blood analysis according to claim 1, further comprising a hydrodynamic focusing unit installed in the two-layer chip system in front, in a direction of fluid flow, of the fluid rotation arrangement.

4. The arrangement for the individualized in-vitro patient blood analysis according to claim 1, further comprising a hydrodynamic focusing unit installed in the two-layer chip system behind, in a direction of fluid flow, the fluid rotation arrangement.

5. The arrangement for the individualized in-vitro patient blood analysis according to claim 1, characterized in that the central control and computer unit is provided with an integrated control software.

6. A method for determining a sepsis score of a patient, comprising providing a blood sample of the patient to the common blood sample supply of the arrangement according to claim 1.

\* \* \* \* \*